United States Patent [19]

Dymicky et al.

[11] Patent Number: 4,677,119
[45] Date of Patent: Jun. 30, 1987

[54] ANTICLOSTRIDIAL AGENTS

[75] Inventors: Michael Dymicky, Philadelphia; James L. Smith, North Wales; Marianne Bencivengo, Erdenheim, all of Pa.

[73] Assignee: The United States of America as represented by the Secretary of Agriculture, Washington, D.C.

[21] Appl. No.: 611,042

[22] Filed: May 16, 1984

[51] Int. Cl.$^4$ .................. A01N 37/02; A01N 37/06
[52] U.S. Cl. .................................................. 514/547
[58] Field of Search ..................... 424/313; 514/547

[56] References Cited

U.S. PATENT DOCUMENTS

| | | | |
|---|---|---|---|
| 2,218,181 | 10/1940 | Searle et al. | 424/313 |
| 3,360,375 | 12/1967 | Buddemeyer et al. | 426/24 |
| 4,346,118 | 8/1982 | Islam | 426/335 |

OTHER PUBLICATIONS

Chemical Abstracts 71:125784.
Chemical Abstracts Registry Handbook (CAS).
Chemical Abstracts 99:174406w.
Chemical Abstracts 95:170462f.
Chemical Abstracts 83:59338h.
IFT 81, 41st Annual Mt. & Food Expo.–Jun. 7–10, 1981, Atlanta, Ga.
J. Food Sci, 48 (5) 1574–1575, 1983.
C&EN, 5/10/82, p. 42.
Org. Prop. and Proceed. Int. 15(4), 233–238, 1983.

Primary Examiner—Albert T. Meyers
Assistant Examiner—John M. Kilcoyne
Attorney, Agent, or Firm—M. Howard Silverstein; David G. McConnell; William E. Scott

[57] ABSTRACT

A number of esters of maleic and fumaric acids were found to exhibit potent anticlostridial activity.

16 Claims, No Drawings

ANTICLOSTRIDIAL AGENTS

BACKGROUND OF THE INVENTION

1. Field of the Invention

This invention relates to mono-, di-, and mixed-n-alkyl maleates and fumarates as food preservatives, and more particularly, to the extraordinary anticlostridial activity exhibited by some selected long chain esters.

2. Description of the Art

The methyl, ethyl and propyl dialkyl esters of fumaric acids have been shown to possess antimicrobial activity and methyl and ethyl fumarates were found to exhibit some antibotulinal activity.

SUMMARY OF THE INVENTION

An object of this invention is to provide novel compounds that are potent inhibitors of the growth of *Clostridium botulinum*.

Another object is to provide a method of preventing spoilage in food and other products.

A further object is to provide a method of treating foods so they can be stored safely for extended periods of time.

According to this invention, the above objects are accomplished by a number of mono-, di-, and mixed n-alkyl maleates and fumarates and their use as inhibitors of the growth of *Clostridium botulinum*. The objects are especially accomplished by the monoalkylesters of maleic and fumaric acids in which the alkyl group of each ester is selected from those alkyl groups containing from 13 to 18 carbon atoms, and by the incorporation of one or more of these esters in foodstuffs in a *Clostridium botulinum* inhibiting effective amount.

DESCRIPTION OF THE INVENTION

A number of n-alkyl esters of maleic and fumaric acids were found to exhibit some anticlostridial activity. However, the minimum inhibitory concentration (MIC) of these esters is, in many cases, 1.5 to 2.0 times that of sodium nitrite. Although the amounts of these compounds required to protect food products from the deleterious effects of *Clostridium botulinum* may be considered high, the compounds have the advantage of being essentially nontoxic and useable in place of sodium nitrite and ethylene dibromide which are known to have carcinogenic properties.

The main focus of our invention is our discovery that certain esters of maleic and fumaric acids are very potent inhibitors of the growth of *Clostridium botulinum*. In fact, some of them are 1000 times more active, that is, their MIC is 1000 times less, than sodium nitrite.

As shown in the table, the n-monoalkylmaleates and n-monoalkylfumarates in which the ester moiety has a 13 to 18 carbon atom chain length are very potent inhibitors of the growth of *Clostridium botulinum*. The MIC for these compounds ranges from 0.2 to 3.1 µg/ml. The n-dialkylfumarates and the n-methylalkylfumarates which have ester moieties in the same chain length range as those of the monoalkyl compounds are generally more potent than sodium nitrite in anticlostridial activity, but they are not comparable in activity to the highly potent monoalkylmaleates and fumarates.

Since the compounds of this invention do not present a problem with regard to toxicity and have extremely low MIC values, they are excellent compositions to use in place of sodium nitrite and ethylene dibromide in the preservation of a variety of foodstuffs.

TABLE

| | HC—COOR<br>‖<br>HC—COOH | ROOC—C—H<br>‖<br>H—C—COOH | ROOC—C—H<br>‖<br>H—C—COOR | CH$_3$OOC—C—H<br>‖<br>H—C—COOR |
|---|---|---|---|---|
| R | MIC µg/ml | MIC µg/ml | MIC µg/ml | MIC µg/ml |
| CH$_3$ | 400 | >400 | 400 | — |
| C$_2$H$_5$ | 300 | >400 | 400 | 400 |
| C$_3$H$_7$ | 300 | >400 | >400 | 400 |
| C$_4$H$_9$ | 300 | >400 | 400 | 400 |
| C$_5$H$_{11}$ | 200 | >400 | 200 | 100 |
| C$_6$H$_{13}$ | 200 | >400 | 100 | 100 |
| C$_7$H$_{15}$ | 200 | 300 | >400 | 100 |
| C$_8$H$_{17}$ | 200 | 150 | >400 | 100 |
| C$_9$H$_{19}$ | 100 | 12.5 | >400 | 50 |
| C$_{10}$H$_{21}$ | 50 | 6.2 | >400 | 25 |
| C$_{11}$H$_{23}$ | 25 | 6.2 | >400 | 12.5 |
| C$_{12}$H$_{25}$ | 25 | 12.5 | >400 | 6.2 |
| C$_{13}$H$_{27}$ | 12.5 | 2.4 | >400 | 12.5 |
| C$_{14}$H$_{29}$ | 3.1 | 1.3 | >40 | 25 |
| C$_{15}$H$_{31}$ | 1.6 | 0.5 | >40 | 50 |
| C$_{16}$H$_{33}$ | 0.8 | 0.4 | >40 | 100 |
| C$_{17}$H$_{35}$ | 0.4 | 0.8 | >40 | 100 |
| C$_{18}$H$_{37}$ | 0.2 | >100 | >40 | 200 |

We claim:

1. A method of protecting foodstuffs comprising inhibiting the growth of *Clostridium botulinum* in said foodstuffs by incorporating into the foodstuff to be protected a *Clostridium botulinum* inhibiting effective amount of a n-monoalkylester of maleic or fumaric acid in which the alkyl group has from 13 to 18 carbon atoms.

2. The method of claim 1 wherein the *Clostridium botulinum* inhibiting effective amount is from 0.2 to 3.1 µg/ml.

3. The method of claim 2 wherein the ester is an n-alkylester of maleic acid.

4. The method of claim 3 wherein the alkyl group of the ester has 14 carbon atoms.

5. The method of claim 3 wherein the alkyl group of the ester has 15 carbon atoms.

6. The method of claim 3 wherein the alkyl group of the ester has 16 carbon atoms.

7. The method of claim 3 wherein the alkyl group of the ester has 17 carbon atoms.

8. The method of claim 3 wherein the alkyl group of the ester has 18 carbon atoms.

9. The method of claim 2 wherein the ester is an n-alkylester of fumaric acid.

10. The method of claim 9 wherein the alkyl group of the ester has 13 carbon atoms.

11. The method of claim 9 wherein the alkyl group of the ester has 14 carbon atoms.

12. The method of claim 9 wherein the alkyl group of the ester has 15 carbon atoms.

13. The method of claim 9 wherein the alkyl group of the ester has 16 carbon atoms.

14. The method of claim 9 wherein the alkyl group of the ester has 17 carbon atoms.

15. A method of protecting foodstuffs comprising inhibiting the growth of *Clostridium botulinum* in said foodstuffs by incorporating into the foodstuff a *Clostridium botulinum* inhibiting effective amount of a methylalkylfumarate in which the alkyl group has from 11 to 13 carbon atoms.

16. The method of claim 15 wherein the alkyl group has 12 carbon atoms.

* * * * *